United States Patent
Takeuchi et al.

(10) Patent No.: US 6,221,634 B1
(45) Date of Patent: Apr. 24, 2001

(54) METHOD FOR PRODUCING XYLITOL OR D-XYLULOSE IN BACTERIA

(75) Inventors: Sonoko Takeuchi; Naoto Tonouchi; Kenzo Yokozeki, all of Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 09/487,308

(22) Filed: Jan. 19, 2000

(30) Foreign Application Priority Data

Jan. 20, 1999 (JP) .................................................. 11-012223

(51) Int. Cl.[7] .............................. C12P 19/00; C12P 19/02; C12P 7/26; C07H 1/00
(52) U.S. Cl. .......................... 435/72; 435/105; 435/148; 435/41; 536/1.11; 536/124; 536/127
(58) Field of Search .............................. 435/156, 41, 105, 435/148, 72; 536/1.11, 124, 127

(56) References Cited

U.S. PATENT DOCUMENTS

| | | | |
|---|---|---|---|
| 3,619,369 | * 11/1971 | Onishi et al. | 435/41 |
| 5,096,820 | 3/1992 | Leleu et al. | 435/158 |
| 5,238,826 | 8/1993 | Leleu et al. | 435/105 |
| 5,631,150 | * 5/1997 | Harkki et al. | 435/105 |

FOREIGN PATENT DOCUMENTS

| | | |
|---|---|---|
| 0 403 392 | 12/1990 | (EP) . |
| 0 421 882 | 4/1991 | (EP) . |
| 0 754 758 | 1/1997 | (EP) . |
| 1166896 | 10/1969 | (GB) . |
| WO 94/10325 | 5/1994 | (WO) . |

OTHER PUBLICATIONS

H. Onishi, et al., Applied Microbiology, vol. 18, No. 6, pp. 1031–1035, "Microbial Production of Xylitol from Glucose," Dec. 1969.

* cited by examiner

Primary Examiner—Deborah Crouch
Assistant Examiner—Quang Nguyen
(74) Attorney, Agent, or Firm—Oblon, Spivak, McClelland, Maier & Neustadt, P.C.

(57) ABSTRACT

Xylitol or D-xylulose is produced through direct fermentation from glucose by culturing a microorganism belonging to the genus Gluconobacter, Acetobacter or Frateuria, and having an ability to produce xylitol or D-xylulose in a suitable medium to accumulate xylitol or D-xylulose in the medium, and collecting xylitol or D-xylulose from the medium.

7 Claims, No Drawings

METHOD FOR PRODUCING XYLITOL OR D-XYLULOSE IN BACTERIA

BACKGROUND OF THE INVENTION

1. Field of the Invention

The present invention relates to novel microorganisms having an ability to produce xylitol or D-xylulose, and a method for producing xylitol or D-xylulose by using a microorganism having an ability to produce xylitol or D-xylulose. D-Xylulose is useful as a material for the production of xylitol, and xylitol is useful as a sweetener in the field of food industry and the like.

2. Description of the Related Art

The demand of xylitol which is a naturally occurring sugar alcohol is expected to increase in future. Xylitol is a promising low-calorie sweetener because it has lower calories and exhibits comparable sweetness compared with sucrose. In addition, because of its anti-dental caries property, it is utilized as a dental caries preventive sweetener. Furthermore, because xylitol does not elevate glucose level in blood, it is utilized for fluid therapy in the treatment of diabetes. For these reasons, it is expected that the demand of xylitol will increase in future.

The current industrial production of xylitol mainly relies on hydrogenation of D-xylose as disclosed in U.S. Pat. No. 4,008,825. D-Xylose used as a raw material is obtained by hydrolysis of plant materials such as trees, straws, corn cobs, oat hulls and other xylan-rich materials.

However, such D-xylose produced by hydrolysis of plant materials suffers a drawback that it is rather expensive, and it is arisen from high production cost. For example, the low yield of the hydrolysis treatment of plant materials leads to low purity of the produced D-xylose. Therefore, the acid used for the hydrolysis and the dyes must be removed by ion exchange treatment after the hydrolysis treatment, and the resulting D-xylose must be further crystallized to remove other hemicellulosic saccharides. In order to obtain D-xylose suitable for foodstuffs, further purification would be required. Such ion exchange treatment and crystallization treatment invite the increase of production cost.

Therefore, several methods for producing xylitol have been developed, which utilize readily available raw materials and generate little waste. For example, there have been developed methods for producing xylitol utilizing other pentitols as a starting material. One of such readily available pentitols is D-arabitol, and D-arabitol can be produced by using yeast (*Can. J. Microbiol.*, 31, 1985, 467–471; *J. Gen. Microbiol.*, 139, 1993, 1047–54). As a method for producing xylitol by utilizing D-arabitol as a raw material, there can be mentioned the method reported in *Applied Microbiology.*, 18, 1969, 1031–1035, which comprises producing D-arabitol from glucose by fermentation using *Debaryomyces hansenii* ATCC20121, then converting the D-arabitol into D-xylulose using *Acetobacter suboxydans*, and converting D-xylulose into xylitol by the action of *Candida guilliermondii* var. soya.

EP 403 392A and EP421 882A disclose methods comprising producing D-arabitol by fermentation using an osmosis-resistant yeast, then converting D-arabitol into D-xylulose using a bacterium belonging to the genus Acetobacter, the genus Gluconobacter, or the genus Klebsiella, forming a mixture of xylose and D-xylulose from the D-xylulose by the action of glucose (xylose) isomerase, and converting the obtained mixture of xylose and D-xylulose into xylitol by hydrogenation. There is also disclosed the production of xylitol comprising preliminarily concentrating xylose in the mixture of xylose and D-xylulose and converting the xylose into xylitol by hydrogenation.

However, those methods for the production of xylitol mentioned above utilize D-arabitol produced by fermentation as a starting material, and convert it by multiple process steps. Therefore, the processes are complicated, and less satisfactory ones in view of process economy compared with the methods based on extraction.

Accordingly, there has been desired a microorganism which has an ability to produce xylitol or D-xylulose through a single step by fermentation starting from glucose as used in the production of other saccharides and sugar alcohols. However, such a bacterium having an ability to produce xylitol or D-xylulose has not been reported so far.

On the other hand, breeding of xylitol fermenting bacteria has been attempted by using gene manipulation techniques. International Publication WO94/10325 discloses production of xylitol from glucose by fermentation by using a recombinant microorganism obtained by introducing an arabitol dehydrogenase gene derived from a bacterium belonging to the genus Klebsiella and a xylitol dehydrogenase gene derived from the genus Pichia into an arabitol fermenting microorganism (yeast belonging to the genus Candida, the gunus Torulopsis, or the genus Zygosaccharomyces). However, while production of 15 g/L of xylitol from 400 g/L of glucose has been reported for the aforementioned recombinant microorganism, it does not reach a practically useful accumulation level. Moreover, the aforementioned recombinant microorganism is introduced with a gene derived from a different species, and therefore information about its safety cannot be considered sufficient.

SUMMARY OF THE INVENTION

The present invention has been accomplished in view of the aforementioned state of the art, and an object of the present invention is to provide a method for producing xylitol or D-xylulose by utilizing a microorganism having an ability to produce xylitol or D-xylulose from glucose by fermentation.

In order to achieve the aforementioned object, the inventors of the present invention searched for a microorganism having an ability to produce xylitol or D-xylulose from glucose by fermentation. As for the direct production of sugar alcohols by fermentation of microorganisms such as yeasts, there have also been reported production of glycerol by using *Zygosaccharomyces acidifaciens* (Arch. Biochem., 7, 257–271 (1945)), production of erythritol by using a yeast belonging to the genus Trychosporonoides (Trychosporonoides sp., Biotechnology Letters, 15, 240–246 (1964)) and so on, in addition to the aforementioned arabitol fermentation. All of these yeasts having an ability to produce sugar alcohol show osmophilicity, i.e., good growth in a culture medium of high osmotic pressure. Therefore, while any microorganisms having an ability to produce xylitol had not been found among the osmophilic yeasts, the inventors of the present invention considered that a novel microorganism having an ability to produce xylitol should exist among osmophilic microorganisms, and extensively screened osmophilic microorganisms. As a result, the inventors already found microorganisms having an ability to produce xylitol and D-xylulose from glucose among osmophilic microorganisms, and those microorganisms are analogous to known acetic acid bacteria (Japanese Patent Application No. 10-193472).

Based on the above findings, the inventors of the present invention further searched for a microorganism having an ability to produce xylitol or D-xylulose among acetic acid bacteria and analogous bacteria. As a result, they found microorganisms belonging to the genus Gluconobacter, Acetobacter, or Frateuria, and having an ability to produce xylitol or D-xylulose from glucose. Thus, they accomplished the present invention.

That is, the present invention provides a method for producing xylitol or D-xylulose, which comprises culturing a microorganism belonging to the genus Gluconobacter, Acetobacter or Frateuria and having an ability to produce xylitol or D-xylulose from glucose in a suitable medium to accumulate xylitol or D-xylulose in the medium, and collecting xylitol or D-xylulose from the medium.

In a preferred embodiment of the aforementioned method for producing xylitol or D-xylulose according to the present invention, the microorganism belonging to the genus Gluconobacter is selected from *Gluconobacter cerinus* or *Gluconobacter oxydans*, the microorganism belonging to the genus Acetobacter is selected from *Acetobacter aceti*, *Acetobacter liquefaciens* or *Acetobacter pasteurianus*, and the microorganism belonging to the genus Frateuria is *Frateuria aurantia*.

According to the present invention, xylitol or D-xylulose can efficiently be produced from cheap raw materials such as glucose.

DETAILED DESCRIPTION OF THE INVENTION

Hereafter, the present invention will be explained in more detail.

The microorganism used for the present invention is a microorganism belonging to the genus Gluconobacter, Acetobacter or Frateuria, and having an ability to produce xylitol or D-xylulose from glucose.

As such a microorganism mentioned above, there can be specifically mentioned *Gluconobacter cerinus*, *Gluconobacter oxydans*, *Acetobacter aceti*, *Acetobacter liquefaciens*, *Acetobacter pasteurianus*, *Frateuria aurantia* and so forth.

As specific strains of the microorganism used for the present invention, the following strains can be listed.

*Gluconobacter cerinus* IFO3262
*luconobacter oxydans* ATCC8147
*Gluconobacter oxydans* IFO3293
*Gluconobacter oxydans* IAM1839
*Gluconobacter oxydans* IFO3250
*Gluconobacter oxydans* IFO3292
*Gluconobacter oxydans* IFO3294
*Gluconobacter oxydans* subsp. oxydans IFO3189
*Gluconobacter oxydans* subsp. suboxydans IFO3172
*Gluconobacter oxydans* subsp. suboxydans IFO3130
*Acetobacter aceti* subsp. xylinum ATCC14851
*Acetobacter liquefaciens* ATCC14835
*Acetobacter pasteurianus* IFO3222
*Acetobacter pasteurianus* IFO3223
*Frateuria aurantia* IFO3245
*Gluconobacter oxydans* ATCC8147, *Acetobacter aceti* subsp. xylinum ATCC14851 and *Acetobacter liquefaciens* ATCC14835 are available from the American Type Culture Collection; 12301 Parklawn Drive, Rockville, Md. 20852, the United States of America.
*Gluconobacter cerinus* IFO3262, *Gluconobacter oxydans* IFO3293, *Gluconobacter oxydans* IFO3250, *Gluconobacter oxydans* IFO3292, *Gluconobacter oxydans* IFO3294, *Gluconobacter oxydans* subsp. oxydans IFO3189, *Gluconobacter oxydans* subsp. suboxydans IFO3172, *Gluconobacter oxydans* subsp. suboxydans IFO3130, *Acetobacter pasteurianus* IFO3222, *Acetobacter pasteurianus* IFO3223, and *Frateuria aurantia* IFO3245 are available from the Institute for Fermentation, Osaka; 17–85, Juso-honmachi 2-chome, Yodogawa-ku, Osaka 532, Japan.

*Gluconobacter oxydans* IAM1839 is available from the Institute of Molecular and Cellular Biosciences (formerly, the Institute of Applied Microbiology), the University of Tokyo; Yayoi 1-chome, Bunkyo-ku, Tokyo, Japan.

Xylitol and/or D-xylulose can be produced by culturing a microorganism having an ability to produce xylitol or D-xylulose from glucose such as those mentioned above in a suitable medium to accumulate xylitol or D-xylulose, or both of them, in the medium, and collecting xylitol and/or D-xylulose from the medium.

The target product produced by the method of the present invention may be either xylitol or D-xylulose, or may be both of them.

Any of the aforementioned microorganisms can suitably be used for the production of D-xylulose. For the production of xylitol, although any of the aforementioned microorganisms can suitably be used, microorganisms belonging to the genus Gluconobacter or Acetobacter are preferred. Specifically, *Gluconobacter cerinus*, *Gluconobacter oxydans*, *Acetobacter aceti*, *Acetobacter liquefaciens*, and *Acetobacter pasteurianus* are preferred for the production of xylitol. As specific strains, the following strains are preferred for the production of xylitol.

*Gluconobacter cerinus* IFO3262
*Gluconobacter oxydans* ATCC8147
*Gluconobacter oxydans* IFO3292
*Gluconobacter oxydans* subsp. suboxydans IFO3130
*Acetobacter aceti* subsp. xylinum ATCC14851
*Acetobacter liquefaciens* ATCC14835
*Acetobacter pasteurianus* IFO3222
*Acetobacter pasteurianus* IFO3223

For the present invention, any variant or mutant strains obtained from microbial strains belonging to the genus Gluconobacter, Acetobacter or Frateuria, and having an ability to produce xylitol or D-xylulose from glucose may be used. Such mutant strains include those obtained by UV exposure, N-methyl-N'-nitro-N-nitrosoguanidine (NTG) treatment, ethyl methanesulfonate (EMS) treatment, nitrous acid treatment, acridine treatment and the like, genetic recombinant strains obtained by genetic engineering techniques such as cell fusion and genetic recombination and so forth.

The medium for culturing the aforementioned microorganisms may be a usual medium containing usual carbon source, nitrogen source, inorganic ions, as well as organic nutrients as required.

As the carbon source, carbohydrates such as glucose, alcohols such as glycerol, organic acids and so forth can be used suitably. In view of the preference observed in the known methods for the production of xylitol, for example, the method for producing xylitol from pentitols such as D-xylose and D-arabitol, a main carbon source is preferably selected from hexoses such as glucose and fructose, disaccharides such as sucrose and lactose, or polysaccharides such as starch. These main carbon source materials are used in the medium in an amount of 10–60%, preferably 20–50%. These carbon sources may be added to the medium at one time, or divided into portions and added portionwise over the time course of the cultivation.

As the nitrogen source, ammonia gas, aqueous ammonia, ammonium salts and so forth may be used. As the inorganic ions, magnesium ions, phosphate ions, potassium ions, iron ions, manganese ions and so forth may be used as required. As the organic nutrient, vitamins, amino acids and materials containing them such as lever extract, yeast extract, malt extract, peptone, meat extract, corn steep liquor, casein decomposition product and so forth may suitably be used.

The culture conditions are also not particularly limited. However, the microorganisms may usually be cultured at a limited pH and temperature selected within the pH range of 5–8 and the temperature range of 25–40° C. The cultivation is performed under an aerobic condition realized by, for example, stirring or shaking. As for the culture time, the microorganisms are desirably cultured until the main carbon source is consumed, i.e., usually for 3–8 days.

Xylitol and/or D-xylulose produced in the medium as described above is separated and collected from the culture in a conventional manner. Specifically, after the solid matter is removed from the culture by centrifugation, filtration or the like, the residual solution can be decolorized and desalted by using activated carbon, ion-exchange resin or the like, and xylitol and/or D-xylulose can be crystallized from the solution. The procedures of the separation and collection of xylitol and/or D-xylulose from culture are easier than the separation from plant material hydrolysates because of lower content of impurities.

The produced D-xylulose can be converted into xylitol by hydrogenation, which can be performed in a known manner.

BEST MODE FOR CARRYING OUT THE INVENTION

The present invention will be explained more specifically with reference to the following examples. However, the present invention is not limited to these examples. In the examples, the produced xylitol and D-xylulose were analyzed by high performance liquid chromatography (HPLC) under the following conditions.

Column: Shodex SC1011 (product of Showa Denko)

Mobile phase: 20% acetonitrile/80% 50 ppm aqueous solution of Ca-EDTA

Flow rate: 1.0 ml/minute

Temperature: 75° C.

Detection: RI detector

A medium containing 0.2% of ammonium sulfate, 0.1% of potassium dihydrogenphosphate, 0.3% of dipotassium hydrogenphosphate, 0.05% of magnesium sulfate and 0.5% of yeast extracts (pH 6.0) was introduced into test tubes in an amount of 4 ml for each tube, and sterilized by heating at 120° C. for 20 minutes. Separately sterilized D-glucose was added to the medium at a concentration of 5%. The aforementioned concentrations (%) are indicated in w/v %.

Each of strains mentioned in Table 1 was inoculated to the aforementioned medium, and cultured at 30° C. for 1 day with shaking. The obtained culture was used as seed culture. The medium having the same composition as mentioned above (except for D-glucose) was introduced into 500-ml Sakaguchi flasks in an amount of 50 ml for each flask, and sterilized by heating at 120° C. for 20 minutes. Separately sterilized glucose and calcium carbonate were added to the medium at a concentration of 5% and 4% respectively. The seed culture was inoculated into this medium at a concentration of 2%, and cultured at 30° C. for 4 days with shaking. Then, after the bacterial cells were removed by centrifugation, xylitol and D-xylulose produced in the medium were quantified by HPLC. The results are shown in Table 1.

TABLE 1

| Strain | Produced xylitol (g/l) | Produced D-xylulose (g/l) |
| --- | --- | --- |
| *Gluconobacter cerinus* IFO3262 | 0.3 | 1.11 |
| *Gluconobacter oxydans* ATCC8147 | 0.4 | 0.4 |
| *Gluconobacter oxydans* IFO3293 | ND* | 1.0 |
| *Gluconobacter oxydans* IAM1839 | ND | 0.5 |
| *Gluconobacter oxydans* IFO3250 | ND | 0.5 |
| *Gluconobacter oxydans* IFO3292 | 0.3 | 1.0 |
| *Gluconobacter oxydans* IFO3294 | ND | 1.0 |
| *Gluconobacter oxydans* subsp. *oxydans* IFO3189 | ND | 1.0 |
| *Gluconobacter oxydans* subsp. *suboxydans* IFO3172 | ND | 0.5 |
| *Gluconobacter oxydans* subsp. *suboxydans* IFO3130 | 0.4 | 1.2 |
| *Acetobacter aceti* subsp. *xylinum* ATCC14851 | 0.5 | 1.6 |
| *Acetobacter liquefaciens* ATCC14835 | 0.5 | 1.1 |
| *Acetobacter pasteurianus* IFO3222 | 0.4 | 1.0 |
| *Acetobacter pasteurianus* IFO3223 | 0.3 | 2.3 |
| *Frateuria aurantia* IFO3245 | ND | 0.8 |

*: ND means "not determined".

What is claimed is:

1. A method for producing xylitol or D-xylulose, comprising:

culturing in a suitable medium a microorganism belonging to the genus Gluconobacter, Acetobacter or Frateuria wherein said microorganism produces xylitol or D-xylulose from glucose, to accumulate xylitol or D-xylulose in the medium, and collecting xylitol or D-xylulose from the medium.

2. The method according to claim 1, wherein the microorganism belonging to the genus Gluconobacter is selected from *Gluconobacter cerinus* or *Gluconobacter oxydans*, the microorganism belonging to the genus Acetobacter is selected from *Acetobacter aceti*, *Acetobacter liquefaciens* or *Acetobacter pasteurianus*, and the microorganism belonging to the genus Frateuria is *Frateuria aurantia*.

3. The method of claim 1, wherein said microorganism belongs to the genus Gluconobacter.

4. The method of claim 1, wherein said microorganism belongs to the genus Acetobacter.

5. The method of claim 1, wherein said microorganism belongs to the genus Frateuria.

6. The method of claim 1, wherein said method produces xylitol.

7. The method of claim 1, wherein said method produces D-xylulose.

* * * * *